United States Patent
Pekar et al.

(10) Patent No.: US 6,378,552 B1
(45) Date of Patent: Apr. 30, 2002

(54) DUAL SPEED FLOW CONTROL VALVE

(75) Inventors: Robert W. Pekar, Florence, MA (US); Rolf Schild, London (GB)

(73) Assignee: Dielectrics Industries, Inc., Chicopee, MA (US)

( * ) Notice: Subject to any disclaimer, the term of this patent is extended or adjusted under 35 U.S.C. 154(b) by 0 days.

(21) Appl. No.: 09/710,986

(22) Filed: Nov. 10, 2000

(51) Int. Cl.⁷ .................. F16K 15/20; A61B 17/135
(52) U.S. Cl. .................. 137/512.4; 137/223; 137/493; 137/493.1; 137/843; 5/655.3; 446/224; 128/DIG. 20
(58) Field of Search .................. 137/223, 512, 137/512.4, 493, 843, 493.1; 5/652.2, 655.3; 128/DIG. 20; 297/DIG. 8; 501/150, 152; 606/202; 446/224

(56) References Cited

U.S. PATENT DOCUMENTS

| | | | |
|---|---|---|---|
| 1,068,167 A | 7/1913 | Philblade | |
| 2,576,637 A | 11/1951 | Patriquin | 277/61 |
| 2,816,571 A | 12/1957 | Pike | 137/493.6 |
| 2,989,073 A | 6/1961 | Goodwin | 137/493.8 |
| 3,118,596 A | 1/1964 | Saile | 230/160 |
| 3,584,671 A | * 6/1971 | Kampa | 137/223 |
| 3,722,526 A | 3/1973 | Henningsson | 137/107 |
| 3,752,148 A | 8/1973 | Schmalzbach | 128/2.05 |
| 3,791,407 A | 2/1974 | Nicholls | 137/512.15 |
| 3,825,008 A | 7/1974 | Shook | 128/327 |
| 3,887,213 A | 6/1975 | Goetz | 280/150 AB |
| 3,906,937 A | 9/1975 | Aronson | 128/2.05 |
| 4,066,084 A | 1/1978 | Tillander | 128/327 |
| 4,310,013 A | 1/1982 | McClaskey | 137/145 |
| 4,552,133 A | 11/1985 | Kawaguchi | 128/44 |
| 4,572,205 A | 2/1986 | Sjonell | 128/686 |
| 4,621,383 A | * 11/1986 | Gendala | 5/655.3 |
| 4,633,910 A | 1/1987 | Sugimura | 138/30 |
| 4,674,532 A | 6/1987 | Koyanagi | 137/512.15 |
| 4,708,167 A | 11/1987 | Koyanagi | 137/512.15 |
| 4,917,646 A | 4/1990 | Kieves | 446/224 |
| 4,920,971 A | 5/1990 | Blessinger | 128/679 |
| 4,938,226 A | 7/1990 | Danielsson et al. | 128/679 |
| 5,022,109 A | * 6/1991 | Pekar | 5/706 |
| 5,144,708 A | 9/1992 | Pekar | 5/454 |
| 5,248,275 A | 9/1993 | McGrath et al. | 446/224 |
| 5,295,892 A | * 3/1994 | Felton | 446/224 |
| 5,372,487 A | 12/1994 | Pekar | 417/480 |
| 5,496,262 A | 3/1996 | Johnson, Jr. et al. | 601/152 |
| 5,564,143 A | 10/1996 | Pekar et al. | 5/708 |
| 5,584,853 A | 12/1996 | McEwen | 606/201 |
| 6,196,260 B1 | 3/2001 | Pekar | 137/512.15 |

FOREIGN PATENT DOCUMENTS

| | | |
|---|---|---|
| DE | 40 30 717 A 1 | 4/1992 |
| FR | 1.180.487 | 12/1958 |

* cited by examiner

Primary Examiner—A. Michael Chambers
Assistant Examiner—Ramesh Krishnamurthy
(74) Attorney, Agent, or Firm—Cantor Colburn LLP

(57) ABSTRACT

An exemplary embodiment of the invention is a dual speed air control valve including a first sheet having an aperture therein and a second sheet continuously secured to the first sheet along a periphery of the first and second sheets. Further, a third sheet in continuously secured to the second sheet along a periphery of the third and second sheets. The first sheet defines at least one aperture in fluid communication with the third sheet. The third sheet defines at least one aperture in fluid communication with the first sheet.

12 Claims, 5 Drawing Sheets

DUAL SPEED FLOW CONTROL VALVE

BACKGROUND

The present invention relates to inflatable bladders and more particularly, to a valve formed of layers of sheet material for controlling the inflation and deflation of an inflatable bladder.

Inflatable structures are known in the art and are used in many applications, such as seat cushions, mattresses and medical devices. Many of these structures require that the rates of inflation and deflation differ. Complex mechanical valves have been devised in an effort to control the rate of inflation and deflation of certain inflatable structures. In other structures several pumps are employed to control the rates of inflation and deflation.

SUMMARY OF THE INVENTION

An exemplary embodiment of the invention is a dual speed flow control valve including a first sheet having an aperture therein and a second sheet continuously secured to the first sheet along a periphery of the first and second sheets. Further, a third sheet is continuously secured to the second sheet along a periphery of the third and second sheets. The first sheet includes at least one aperture. The third sheet includes at least one aperture.

BRIEF DESCRIPTION OF THE DRAWINGS

Referring now to the drawings, wherein like elements are numbered alike in the several figures.

DETAILED DESCRIPTION

Figure 1:
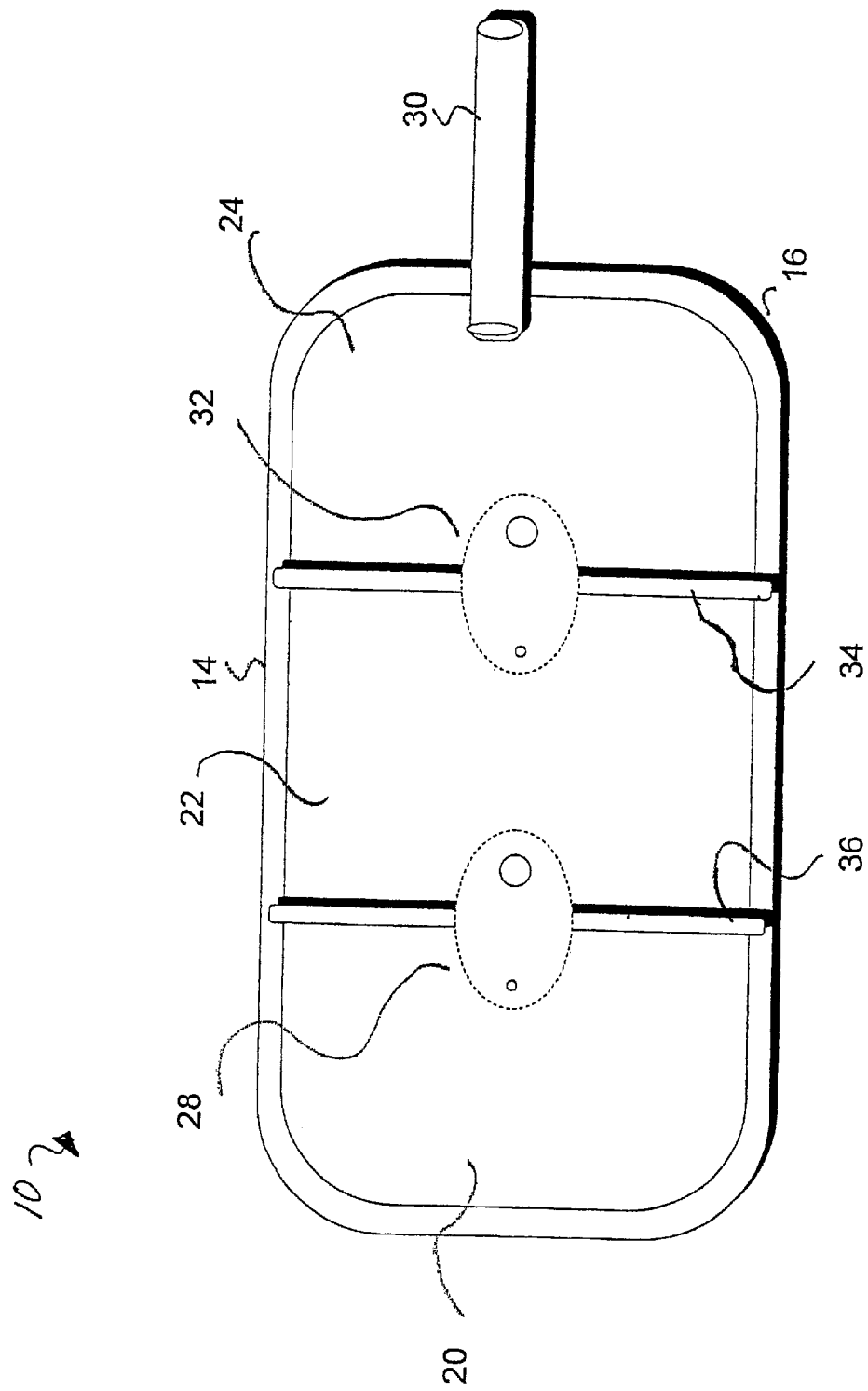
FIG. 1 is an exemplary top plan view of a three-chambered bladder including two dual speed flow control valves.

Referring to FIG. 1, it is seen that a multi-chambered bladder 10 is illustrated. Multi-chambered bladder 10 comprises two layers of sheet material 14, 16 sealed together to form three of chambers 24, 22 and 20. The chambers 24, 22 and 20 will be referred to as first, second and third respectively. The bladder 10 is a single cell that is divided by two internal seams 34, 36. The bladder is inflatable with any fluid including air. Valves 28, 32 are attached to each seams 34, 36 to allow for a staged inflation of each of chambers 24, 22 and 20 of the single bladder 10. The object of the valves 28, 32 is to achieve a staged pressure within bladder 10. As described herein, chamber 24 inflates faster than chamber 22. Likewise, chamber 22 inflates faster than chamber 20. Bladder 10 may be used for a medical device having the objective to apply pressure. For example, this device can be used to stimulate blood flow from a distal to a proximal end of a limb, such as an arm or a leg. Staged pressure is known to stimulate blood circulation. The staged pressure within the bladder begins when bladder 10 is inflated through an input port 30. Conversely, valves 28, 32 allow chambers 24, 22 and 20 of the bladder 10 to deflate rapidly at similar rates. When chambers 24, 22 and 20 have deflated the next cycle of pressurization is set to start with all three chambers at zero pressure. Historically one would use the three independent chambers and a timed pumping cycle to achieve a staged pressure bladder. Valves 28 and 32 allow for a single, unified divided bladder with a simple pumping system.

As discussed above, the bladder 10 is formed of two layers 14, 16 comprising sheet material, such as heat sealable thermoplastic material, superimposed on each other and heat sealed continuously about its periphery. The seams 34, 36 are sealed between the two layers 14, 16 to form chambers 24, 22 and 20 and are interconnected by dual speed flow control valves 28, 32.

Flow control valves 32, 28 are sealed to the inner surfaces of the seams 34, 36. The inner surfaces of the 110 and 114 sheets, that comprise the flow control valves 28, 32, are coated with a release material 118 that prevents fusion of the three sheets to each other, as well as, to the walls of the bladder during the manufacturing process. Valve 32 restricts the air-flow passing from the first chamber 24 to the second chamber 22, thereby inflating the first chamber 24 faster than the second chamber 22. Further, control valve 32 allows the second chamber 22 to deflate at a faster rate.

Figure 2:
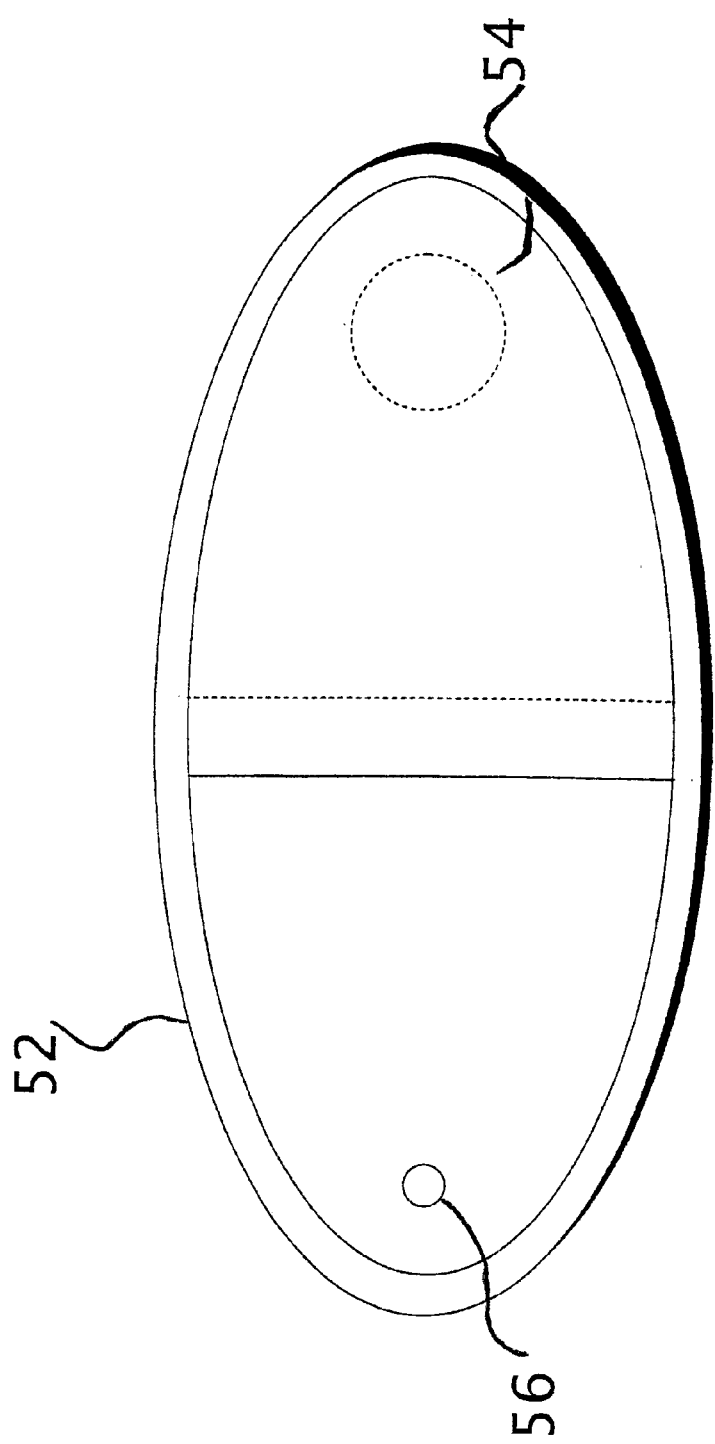
FIG. 2 is an exemplary top plan view of a dual speed flow control valve.
Figure 3:
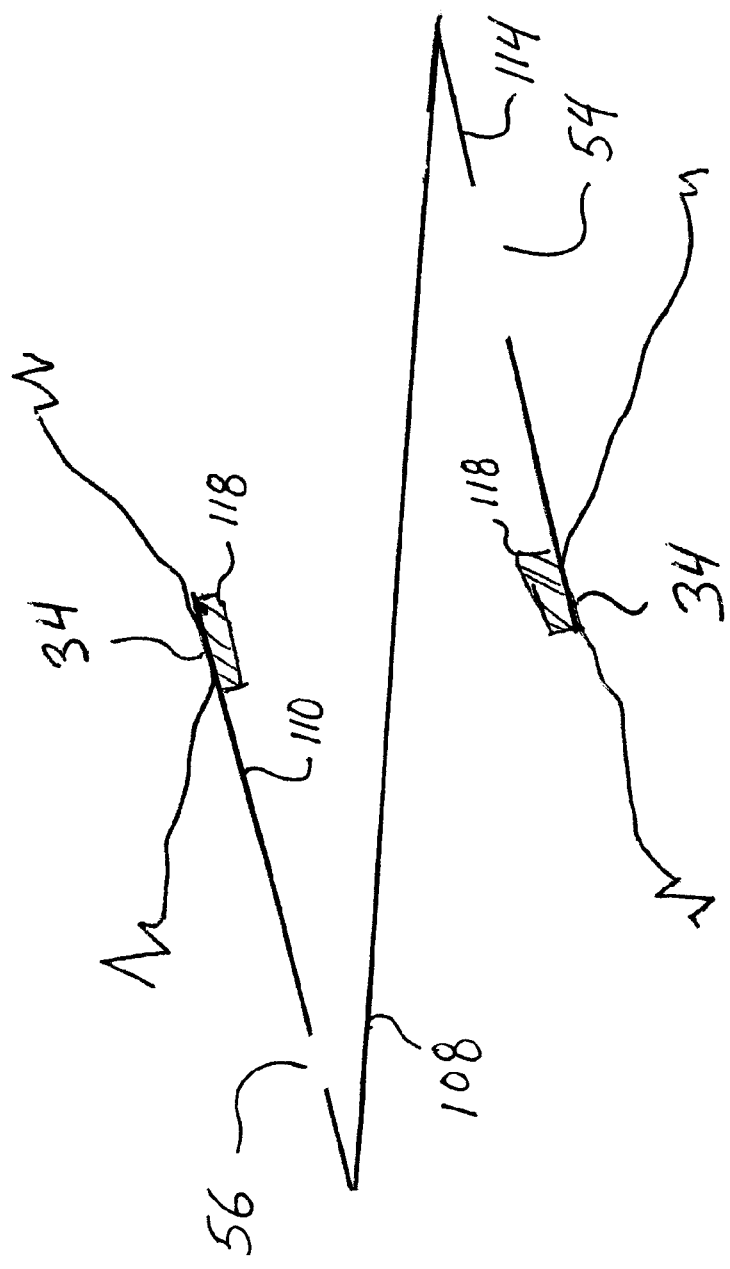
FIG. 3 is an exemplary sectional view of a dual speed flow control valve of FIG. 2.

As best shown in FIGS. 2 and 3, control valves 28, 32 are formed of an upper, middle and lower layer 110, 108 and 114 respectively. These layers are composed of sheet material. Lower layer 114 includes an exhaust aperture 54 disposed therein. Upper layer 110 includes an intake aperture 56 located in registered relations with the lower layer 114. Upper, middle and lower layers 110, 108 and 114 are sealed at predetermined seal locations to form a continuous seal around the valve's periphery 52.

Figure 4:
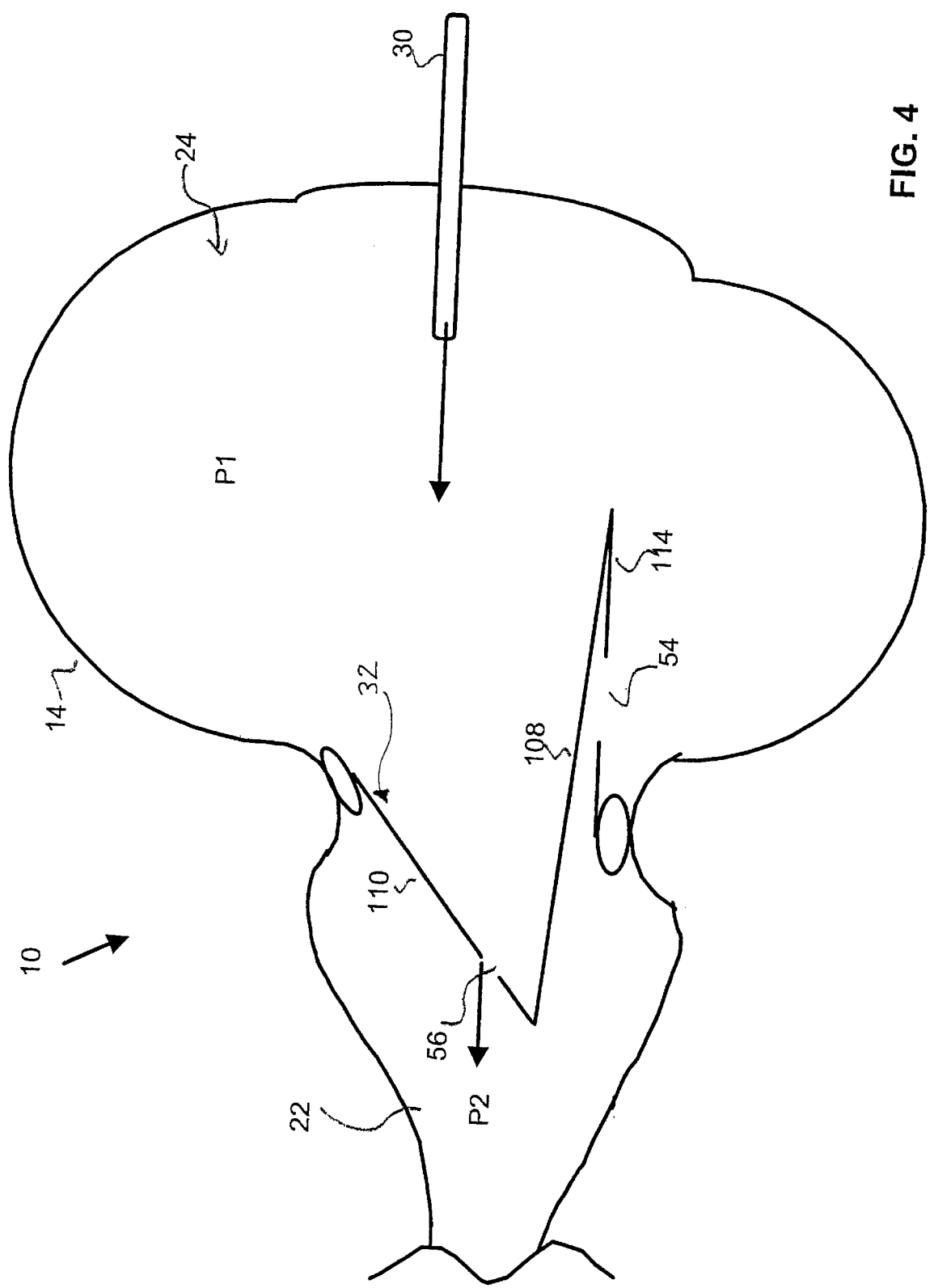
FIG. 4 is an exemplary sectional view of a partially inflated bladder.

During the inflation of the bladder 10 as shown in FIG. 4, flow passes into the first chamber 24 through input port 30. A pressure P1 against valve 32 forces layers 108 and 114 to collapse upon on another thereby forcing all the flow to pass through the intake aperture 56 disposed in the upper layer 110 of dual speed flow control valve 28. Accordingly, intake aperture 56 is in fluid communication with in-coming flow. The diameter of intake aperture 56 determines the rate of inflation or delay of inflation of the adjacent chamber 22. Preferably, intake aperture 56 of dual speed flow control valve 28 is positioned a sufficient distance from outer layer 14 of the bladder 10, which allows for continuous uninterrupted flow from the first chamber 24 to the second chamber 22 as shown by arrow A.

Figure 5:
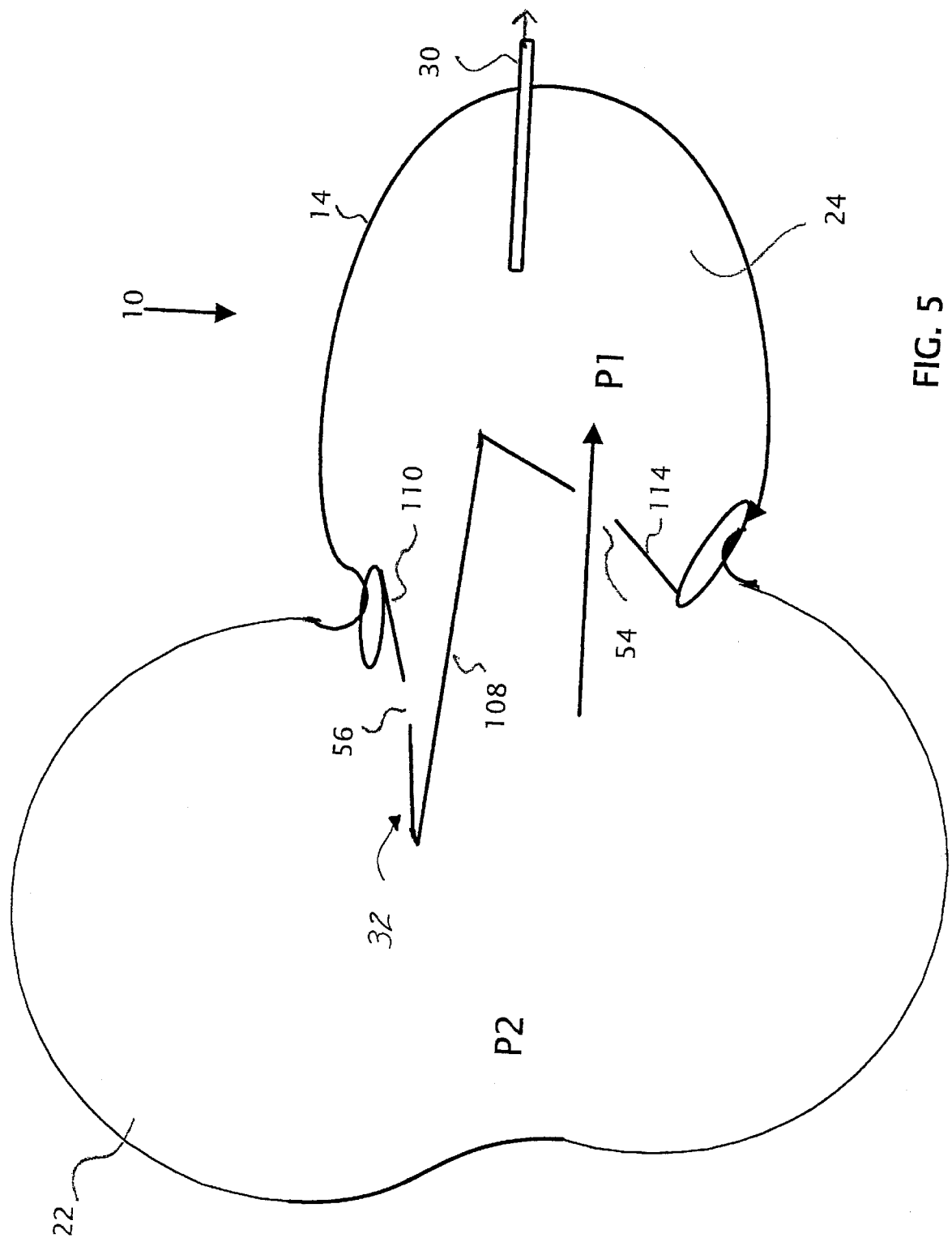
FIG. 5 is an exemplary sectional view of a partially deflated bladder.

During the deflation of the bladder 10 as shown in FIG. 5, the flow from the first chamber 24 deflates at a faster rate, therefore, the pressure P2 in the second chamber 22 becomes greater than the pressure P1 in the first chamber 24. This pressure causes further separation of middle layer 108 from lower layer 114, thereby enhancing the deflation process. Consequently, the air from second chamber 22 exits through a fully exposed exhaust aperture 54. The increased diameter of exhaust aperture 54 of valve 32 facilitates the second chamber 22 to deflate at a significantly higher rate than it inflated. Thus, during deflation the pressure P1 in the first chamber 24 drops quickly.

The rates of inflation of chambers 24, 22 and 20 are dependent upon the cross sectional area of intake aperture 56. Similarly, the rates of deflation of chambers 24, 22 and 20 are dependent upon the cross sectional area of exhaust aperture 54.

It will be understood that a person skilled in the art may make modifications to the preferred embodiment shown herein within the scope and intent of the claims. While the present invention has been described as carried out in a specific embodiment thereof, it is not intended to be limited thereby but is intended to cover the invention broadly within the scope and spirit of the claims.

What is claimed is:

1. A dual speed flow control valve comprising:
   a first sheet having an intake aperture therein;
   a second sheet continuously secured to said first sheet along a periphery of said first sheet and said second sheet;
   a third sheet continuously secured to said second sheet along a periphery of said second sheet and said third sheet; and
   said third sheet having an exhaust aperture therein.

2. The dual speed flow control valve of claim 1 wherein:
   in a first state, said exhaust aperture is closed; and
   in a second state said intake aperture is closed.

3. The dual speed flow control valve of claim 2 wherein:
   said first state occurs when a first pressure acting on a first side of said first sheet is greater than a second pressure acting on a second side of said first sheet.

4. The dual speed flow control valve of claim 2 wherein:
   said second state occurs when a first pressure acting on a first side of said first sheet is less than a second pressure acting on a second side of said first sheet.

5. The dual speed flow control valve of claim 1 wherein:
   an area of said intake aperture is less than the area of said exhaust aperture.

6. An inflatable bladder having chambers comprising:
   a first chamber;
   a second chamber;
   a dual speed flow control valve positioned in said first chamber and said second chamber, said dual speed flow control valve including:
   a first sheet having an intake aperture therein;
   a second sheet secured to said first sheet continuously along a periphery of said first and second sheets;
   a third sheet having an exhaust aperture therein; and
   said third sheet secured to said second sheet continuously along a periphery of said second sheet and said third sheet.

7. The inflatable bladder of claim 6 wherein:
   said dual speed flow control valve is positioned across a seam that partitions said first chamber and said second chamber.

8. The inflatable bladder of claim 6 further comprising:
   a release material that prevents the three layers of the flow control valve from fusing to the outer layer of the bladder or each other.

9. The inflatable bladder of claim 6 wherein:
   in a first state, said exhaust aperture is sealed; and
   in a second state said intake aperture is open.

10. The inflatable bladder of claim 9 wherein:
    said first state occurs when a first pressure acting on a first side of said first sheet is greater than a second pressure acting on a second side of said first sheet.

11. The inflatable bladder of claim 9 wherein:
    said second state occurs when a first pressure acting on a first side of said first sheet is less than a second pressure acting on a second side of said first sheet.

12. The inflatable bladder of claim 6 wherein:
    said inflatable bladder is used to apply pressure to a body of a patient in stages thereby stimulating blood circulation.

* * * * *